United States Patent [19]

Ni et al.

[11] Patent Number: 4,735,805
[45] Date of Patent: Apr. 5, 1988

[54] BISECTABLE DRUG TABLET

[75] Inventors: Phillip F. Ni, Mattawan; Larry F. Odar, Galesburg, both of Mich.

[73] Assignee: The Upjohn Company, Kalamazoo, Mich.

[21] Appl. No.: 24,747

[22] Filed: Mar. 11, 1987

[51] Int. Cl.⁴ ............................................. A61K 9/44
[52] U.S. Cl. ................................. 424/464; 424/467
[58] Field of Search ............................. 424/464, 467

[56] References Cited

U.S. PATENT DOCUMENTS 3,146,169  8/1964  Stephenson et al. ............... 424/467
4,258,027  3/1981  Ullman et al. ..................... 424/467

*Primary Examiner*—Michael R. Lusignan
*Attorney, Agent, or Firm*—Flynn, Thiel, Boutell & Tanis

[57] ABSTRACT

A bisectable drug tablet having an elongated tablet body with a length greater than its width. The tablet body also has top and bottom surfaces with a concavity being provided in each thereof. A breaking groove is formed in at least one of the concavities and extends laterally across the width of the tablet at an apex of the one cavity. Thus, upon application of a downward pressure to either the top or bottom surfaces of the tablet, when the other of the top and bottom surfaces faces downwardly and the opposite longitudinal ends of the tablet rest on a support surface, the tablet will fracture along the groove, the fracture occurring irrespective of whether the breaking groove faces toward or away from the support surface.

2 Claims, 1 Drawing Sheet

BISECTABLE DRUG TABLET

FIELD OF THE INVENTION

This invention relates to a bisectable drug tablet and, more particularly, to a bisectable drug tablet having a length greater than its width and structure for facilitating a breaking of the tablet into two parts independent of the position of the tablet on a support surface.

BACKGROUND OF THE INVENTION

Bisectable drug tablets have been known for many years and are provided to patients to enable them to break the tablet into two or more parts to enable fractional dosages of the medicine to be taken by the patient (see British Patent No. 993 291). Heretofore, problems have been encountered by the patient in facilitating a proper breakage of the tablet into its component parts due to the strength of the binder agent utilized to bind the active pharmacological agents contained within the tablet. Arthritic patients may be unable to break the tablet into its component parts due to the aforesaid strength characteristic. In some instances, a sharp edged tool, such as a knife, is needed in order to effect an even breakage of the tablet into its component parts.

It is an object of the present invention to provide a bisectable drug tablet capable of being easily broken into two parts independent of the orientation of the tablet on a supporting surface.

It is a further object of this invention to provide a bisectable drug tablet, as aforesaid, capable of being broken into its component parts by simply pressing down on the tablet when supported on a support surface.

It is a further object of this invention to provide a bisectable drug tablet, as aforesaid, which has a length greater than its width and appropriate structure at its opposite longitudinal ends as well as structure defining a zone of weakness in the central region to facilitate a breakage of the tablet into separate but equal components.

It is a further object of this invention to provide a bisectable drug tablet, as aforesaid, having the requisite strength characteristics to prevent premature breakage of the tablet either during manufacture, insertion into a container or during transit of the container to the end user.

It is a further object of this invention to provide a bisectable drug tablet, as aforesaid, which is easy to manufacture and is of a sufficient but yet minimum size to facilitate easy swallowing of the tablet by the end user patient.

SUMMARY OF THE INVENTION

The objects and purposes of the broadest aspect of the invention, including those set forth above, are met by providing a bisectable drug tablet having an elongated tablet body with a length greater than its width. The tablet body also has top and bottom surfaces with a concavity being provided in each thereof. A breaking groove is formed in at least one of the concavities and extends laterally across the width of the tablet at an apex of the one cavity. Thus, upon application of a downward pressure to either the top or bottom surfaces of the tablet, when the other of the top and bottom surfaces faces downwardly and the opposite longitudinal ends of the tablet rest on a support surface, the tablet will fracture along the groove, the fracture occurring irrespective of whether the breaking groove faces toward or away from the support surface.

BRIEF DESCRIPTION OF THE DRAWING

The subject matter of the invention will be described in more detail hereinafter in connection with the exemplary embodiment illustrated in the drawing, in which.

DETAILED DESCRIPTION

Figures 1, 2:
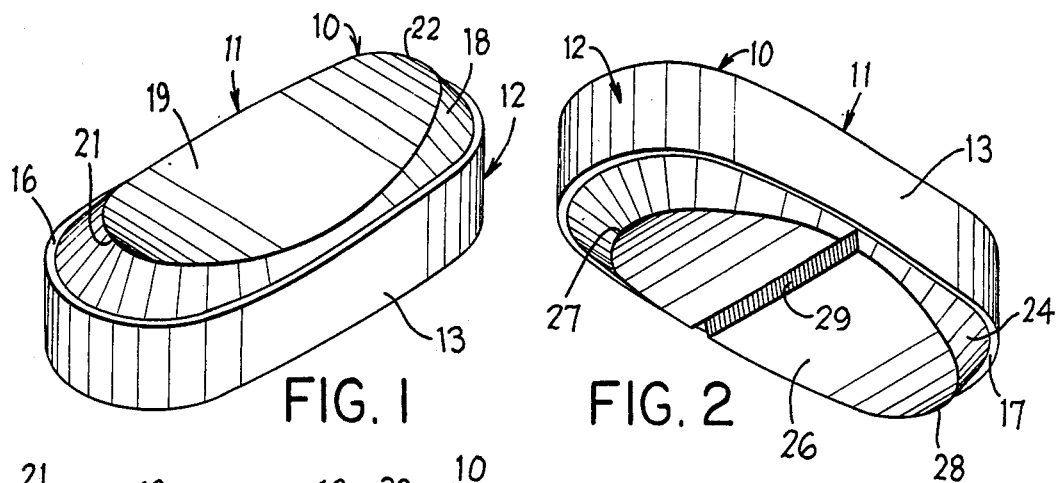
FIG. 1 is a left top perspective view of a bisectable tablet embodying the invention.
FIG. 2 is a left bottom perspective view of the tablet.
Figures 3, 5:
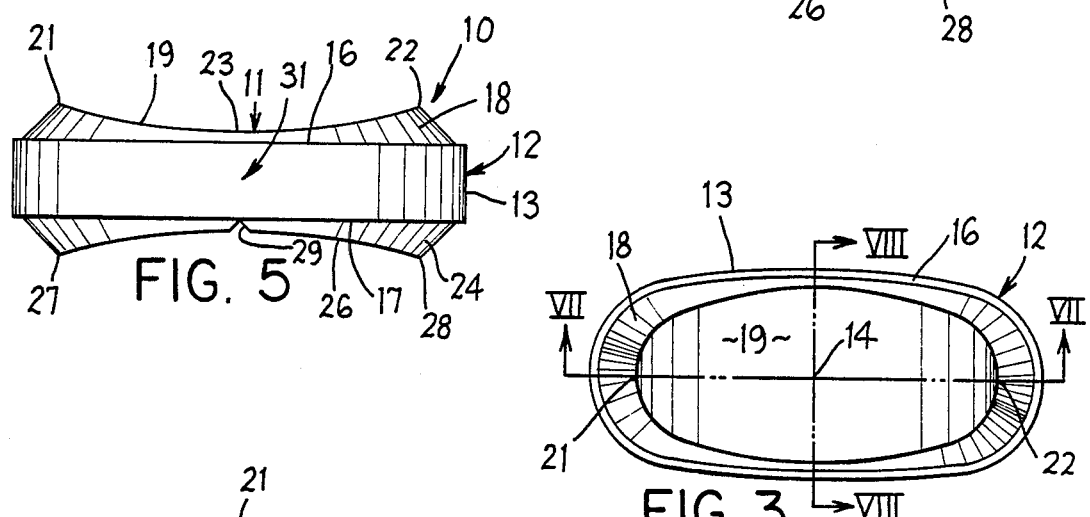
FIG. 3 is a top view thereof.
FIG. 5 is a side view thereof.
Figure 6:
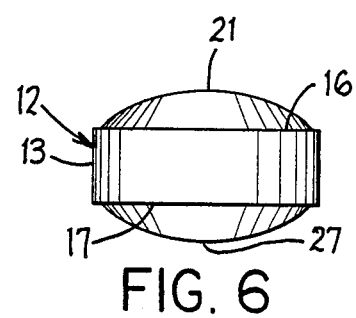
FIG. 6 is an end view thereof.
Figure 4:
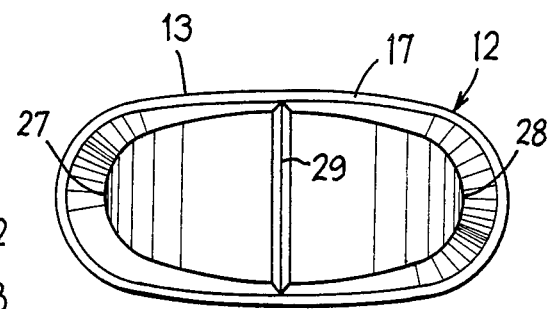
FIG. 4 is a bottom view thereof.

A bisectable drug tablet 10 is illustrated in a perspective view in FIGS. 1 and 2. FIG. 1 illustrates the drug tablet from the top and left end thereof. FIG. 2 illustrates the drug tablet from the bottom and left end thereof. The tablet 10 has an elongated tablet body 11 having a length greater than its width. The tablet body includes an elongated central body part 12 of a finite and uniform thickness and having an outwardly facing, smooth and uninterrupted perimetrical surface 13 extending parallel to a theoretical line 14 (FIG. 3) extending through a geometric center of the tablet. Further characteristics of the theoretical line will be explained in more detail below. The central body part 12 is generally of an oblong, almost eliptical shape as shown in FIGS. 3 and 4. Further, the central body part 12 has a flat top surface 16 and a flat bottom surface 17.

The top surface 16 of the central body part 12 has an upstanding frustoconical-like part 18 thereon. The upper surface of the frustoconical-like part 18 is provided with an arcuately contoured concavity 19. The provision of the arcuate concavity 19 leaves a pair of fulcrum points 21 and 22. Between the fulcrum points 21 and 22, the arcuately contoured concavity 19 extends smoothly and uninterrupted therebetween. The apex 23 of the arcuately contoured concavity 19 is spaced upwardly from the top surface 16 of the central body part 12.

Similarly, the bottom surface 17 of the central body part 12 has an upstanding frustoconical-like part 24 into the top surface of which is provided an arcuately contoured concavity 26. The provision of the arcuately contoured concavity 26 in the top surface of the frustoconical-like part 24 leaves a pair of fulcrum points 27 and 28 at the opposite longitudinal ends. The upwardly facing surface of the arcuately contoured concavity 26 is smooth between the fulcrum points 27 and 28 except for the provision of a breaking groove 29 extending laterally of the tablet in a direction perpendicular to the longitudinal axis of the bisectable drug tablet 10. Further, the breaking groove 29 is located at the apex of the arcuately contoured concavity 26 and the depth of the groove extends to but not beyond the bottom surface 17 of the central body part 12 as illustrated in FIG. 5.

Figure 7:
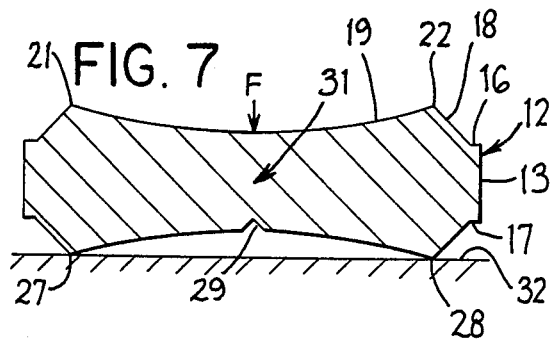
FIG. 7 is a sectional view taken along the line VII—VII of FIG. 3.
Figure 8:
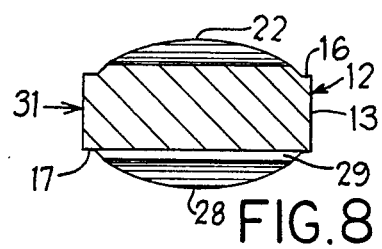
FIG. 8 is a sectional view taken along the line VIII—VIII of FIG. 3.

The spacing between the apex 23 of the arcuately contoured concavity 19 and the bottom of the breaking groove 29 defines a zone of weakness generally referred to by the reference numeral 31. A cross section of the zone of weakness 31 is shown in FIG. 8. Thus, when the tablet is positioned on a support surface 32 (FIG. 7), either the fulcrum points 21 and 22 will rest thereon or the fulcrum points 27 and 28 will rest thereon. As illustrated in FIG. 7, the fulcrum points 27 and 28 rest on the support surface 32. The longitudinal spacing between the breaking groove 29 and the fulcrum points 21, 27 and 22, 28 defines a sufficient lever arm such that when a force F (FIG. 7) is applied to the tablet, breakage will occur at the zone of weakness 31. That is, the strength characteristic of the material of the tablet everywhere in the tablet except for the laterally extending zone of weakness 31, which zone of weakness extends across the full width of the tablet 10, is stronger than the strength characteristic at the zone of weakness 31. This is predominantly due to the cross-sectional area of the tablet taken along the section line VIII—VIII being less than the cross-sectional area of the tablet taken at any other location in the tablet parallel to the aforesaid section line caused by the provision of the breaking groove 29 thereat, and which functions as a stress concentrator.

The theoretical line 14 mentioned above and extending through the geometric center of the tablet 10 extends, when the tablet rests as illustrated in FIG. 7 on a support surface 32, perpendicular to the support surface 32. Further, this theoretical line 14 extends through the central portion of the zone of weakness 31.

The fulcrum points 21 and 27 as well as the fulcrum points 22 and 28 are positioned one above the other when the tablet is positioned as shown in FIG. 7, namely, resting on a support surface 32. It is to be remembered that the tablet 10 can be positioned either as shown in FIG. 7 or totally upsidedown so that the fulcrum point 21 and 22 rest on the support surface 32. The fulcrum point 21 and 27 lie in a plane as do the fulcrum points 22 and 28, which planes extend parallel to each other and the theoretical line 14, but perpendicular to the support surface 32.

When the tablet 10 is placed on a support surface 32 as illustrated in FIG. 7, the arcuately contoured groove 26 forms a bridge between the fulcrum points 27 and 28. No other portion of the tablet 10, other than the fulcrum points 27 and 28, contact the support surface 32.

Although a particular preferred embodiment of the invention has been disclosed in detail for illustrative purposes, it will be recognized that variations or modifications of the disclosed apparatus, including the rearrangement of parts, lie within the scope of the present invention.

The embodiment of the invention in which an exclusive property or privilege is claimed are defined as follows:

1. A bisectable drug tablet, comprising:
   an elongated tablet body having a length greater than its width, said body having top and bottom surfaces;
   first and second concavities, one each on said top and bottom surfaces, each concavity being equal in size and having parallel major and minor axes, said first concavity having a smooth and uninterrupted arcuate surface extending between the opposite longitudinal ends of said body, said opposite longitudinal ends of said body being of a thicker dimension than the thickness of said body measured at apexes of said concavities;
   a breaking groove formed in a second one of said concavities, said breaking groove extending laterally across the width of said tablet at an apex of said second cavity, so that upon application of downward pressure to one of said top and bottom surfaces, when the other of said top and bottom surfaces faces downwardly and said opposite longitudinal ends rest on a support surface, said tablet will fracture along said breaking groove, said fracture occuring irrespective of whether said breaking groove faces toward or away from said support surface.

2. The bisectable drug tablet according to claim 1, wherein said tablet body includes an elongated central body part of a finite and uniform thickness and having an outwardly facing, smooth and uninterrupted perimetrical surface extending parallel to a theoretical line through a geometric center of said table, said theoretical line extending perpendicular to said support surface when said opposite longitudinal ends of said tablet rest on said support surface;
   wherein each top and bottom surface of said central body part has an upstanding frustoconical-like part into each of the tops of which is provided said concavity, the depth of each of said concavities being less than the highest height dimension of said frustoconical parts; and
   wherein said breaking groove has a depth that extends from said apex of said second concavity to one of said top and bottom surfaces of central body part.

* * * * *